United States Patent [19]

Sakai

[11] 4,385,106
[45] May 24, 1983

[54] CHARGE TRANSFER LAYER WITH STYRYL HYDRAZONES

[75] Inventor: Kiyoshi Sakai, Numazu, Japan

[73] Assignee: Ricoh Co., Ltd., Tokyo, Japan

[21] Appl. No.: 235,375

[22] Filed: Feb. 19, 1981

[30] Foreign Application Priority Data

Feb. 28, 1980 [JP] Japan .................................. 55-25069
Feb. 29, 1980 [JP] Japan .................................. 55-25575

[51] Int. Cl.³ .......................... G03G 5/14; G03G 5/04
[52] U.S. Cl. .......................................... 430/59; 430/58
[58] Field of Search .................................. 430/58, 59

[56] References Cited

U.S. PATENT DOCUMENTS 4,150,987 4/1979 Anderson et al. ..................... 430/58
4,256,821 3/1981 Enomoto et al. ................. 430/58 X
4,278,747 7/1981 Murazama et al. ............... 430/58 X Primary Examiner—Roland E. Martin, Jr.
Attorney, Agent, or Firm—Flynn, Thiel, Boutell & Tanis

[57] ABSTRACT

The present invention provides a novel hydrazone compound expressed by the general formula I

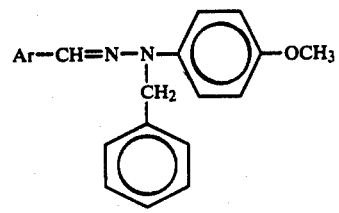

(wherein Ar represents substituted or non-substituted naphthyl group, anthryl group, styryl group, pyridyl group, thienyl group, furyl group or carbazolyl group.);

the process for manufacturing thereof; and a multilayer type electrophotographic element comprising an electrically conductive substrate and a charge carrier generating layer and a charge transfer layer as successively superposed on said substrate, said charge transfer layer containing a hydrazone compound, as effective ingredient, expressed by the general formula II

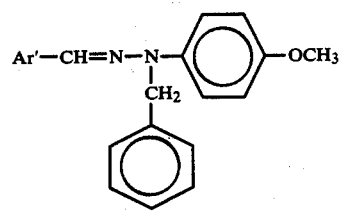

(wherien Ar' represents condensed polycyclic rings such as substituted or non-substituted naphthalene ring, anthracene ring and the like; heterocyclic rings such as substituted or non-substituted furan ring, thiophene ring, pyridine ring, carbazole ring and the like; or substituted or non-substituted styryl group.)

10 Claims, 13 Drawing Figures

CHARGE TRANSFER LAYER WITH STYRYL HYDRAZONES

BACKGROUND OF THE INVENTION

1. Field of the Invention

The present invention relates to a novel hydrazone compound useful as a charge transfer material in an electrophotographic element, which is expressed by the general formula

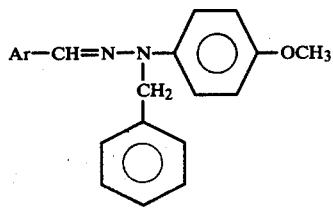

(wherein Ar represents substituted or non-substituted naphthyl group, anthryl group, styryl group, pyridyl group, thienyl group, furyl group or carbazolyl group.);

the process for manufacturing thereof; and the utilization of said compound or analogues thereof for electrophotographic elements.

2. Description of the Prior Art

As conventional photoconductive materials for photosensitive elements useful in electrophotographic systems, there are known inorganic materials such as selenium, cadmium sulfide, zinc oxide and the like. The "electrophotographic system" herein is an image-forming method which generally comprises: charging a photosensitive element with electricity by means of corona discharge in the dark, subsequently imagewise exposing the element to light; selectively dispelling the electric charge of only the light-exposed portions of the element to thereby obtain an electrostatic latent image; and rendering visible this latent image area through a developing means using electroscopic fine particles called toner consisting of a coloring agent such as dyes, pigments, etc. and a binder such as high molecular substances to thereby form an image. To mention the fundamental characteristics required for the photosensitive element in such an electrophotographic method, (1) it should be capable of being charged with electricity to a suitable degree of potential in the dark, (2) it allows little dissipation of the electric charge thereof in the dark, and (3) it should be capable of rapidly dissipating the electric charge thereof when subjected to radiation of light.

The above mentioned conventional inorganic photosensitive elements admittedly have many advantages, but, on the other hand, they have various deficiencies. Accordingly, there have recently been proposed organic photosensitive elements utilizing many kinds of organic materials, and some of them have been put to practical use. Among others, a photosensitive element comprising a material which absorbs light and generates charge carriers (hereinafter called a charge carrier generating material) and a material which accepts charge carriers and transfers them (hereinafter called a charge transfer material) is known to be capable of providing an unprecedentedly high sensitivity because it permits a wide range of selection of materials suitable for every function compared with the photosensitive elements designed for performing the generation of charge carriers and the transfer of charge carriers by means of one and the same material. To mention the requirements for the materials to be used in this kind of photosensitive element, as to said charge carrier generating material, it should be capable of absorbing a desired light and generating charge carriers; it should be capable of displaying a high efficiency in generating charge carriers; it should be easy to treat for preparation of the photosensitive element; and so forth, while as to said charge transfer material, it should be capable of readily accepting charge carriers from the charge carrier generating material; it should permit rapid transfer of charge carriers; it should not show absorption of light in the photosensitive region of the charge carrier generating material; and so forth. Further, it is especially to be noted that the charge transfer material suitable for use in the photosensitive element varies with the charge carrier generating material employed. When the combination of the charge carrier generating material with the charge transfer material is not appropriate, the potential of charged electricity in the dark fails to be sufficient, the resulting image is of low density because of insufficient dissipation of electric charge at the time of radiation of light, and the ground gets stained. Generally speaking, a photosensitive element which has a high potential of charged electricity in the dark tends to be poor in dissipation of the electric charge, while one which shows good dissipation of the electric charge tends to have a low potential of charged electricity, and this tendency varies with the kind of the charge carrier generating material and also the kind of the charge transfer material employed. For practical purposes, an appropriate combination of the charge carrier generating material and the charge transfer material is so selected as to realize dissipation of the charge to such a degree as will not cause stains of the ground and to attain a potential charged to such a degree as will bring about sufficient image densities.

As the above mentioned charge carrier generating materials, there have been proposed a great many substances. To cite especially effective substances, there are CI Pigment Blue 25 (Color Index 21180), azo pigment having carbazole skeleton (as disclosed in Japanese Laid-open Patent Application No. 95033/1978), azo pigment having triphenylamine skeleton, azo pigment having styrylstilbene skeleton (as disclosed in Japanese Laid-open Patent Application No. 13344/1978), azo pigment having diphenyloxadiazole skeleton (as disclosed in Japanese Laid-open Patent Application No. 12742/1979), azo pigment having fluorenone skeleton (as disclosed in Japanese Laid-open Patent Application No. 22834/1979), etc. However, for the foregoing reasons, the charge transfer materials suitable to these charge carrier generating materials are different from one another.

SUMMARY OF THE INVENTION

We have studied a number of charge transfer materials and found that, when the degree of the potential charged and the ease of dissipation of the electric charge are observed from the viewpoint of the chemical constitution of the charge transfer materials, a charge transfer material wherein an electron donor has been introduced is superior in dissipating the electric charge. The present invention has been completed on the basis of this finding.

In other words, a primary object of the present invention is to provide a hydrazone compound expressed by the general formula I

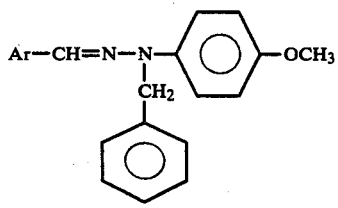

(wherein Ar represents substituted or non-substituted naphthyl group, anthryl group, styryl group, pyridyl group, thienyl group, furyl group or carbazolyl group.)
as a charge transfer material which holds an appropriate potential of charged electricity in the dark and is capable of rapidly dissipating the electric charge when subjected to radiation of light at the time of using it together with various charge carrier generating materials.

Another object of the present invention is to provide a process for manufacturing the foregoing novel hydrazone compound, which is characterized by effecting reaction of aldehydes expressed by the formula Ar-CHO (wherein Ar represents the same as above) with 1-benzyl-1-p-anishydrazine expressed by the formula

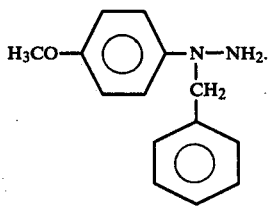

A further object of the present invention is to provide an electrophotographic element which is characterized in that it comprises an electrically conductive substrate and a charge carrier generating layer and a charge transfer layer as superposed on said substrate, said charge transfer layer containing a hydrazone compound, as effective ingredient, expressed by the general formula II

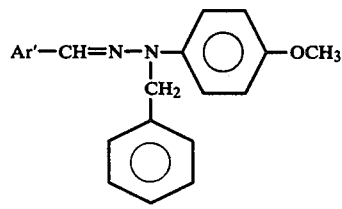

(wherein Ar' represents condensed polycyclic rings such as substituted or non-substituted naphthalene ring, anthracene ring and the like; heterocyclic rings such as substituted or non-substituted furan ring, thiophene ring, pyridine ring, carbazole ring and the like; or substituted or non-substituted styryl group.)

As hydrazones of this kind, there have already been proposed ones expressed by the foregoing general formula I excluding the methoxy group (as disclosed in Japanese Laid-open Patent Application No. 150128/1979, etc.). The charge transfer materials disclosed in these literatures are admittedly effective with respect to a certain kind of charge carrier generating material, but they are not always effective with respect to every charge transfer material. Especially in the case of a charge carrier generating material which can provide only such a combination as will achieve a high potential of charged electricity in the dark and poor dissipation of electric charge when subjected to radiation of light, the hydrazone compounds of the present invention work effectively. These hydrazone compounds are colorless or citrine crystals at normal temperature. In the case of the hydrazone compound expressed by the general formula I, it can be readily prepared by reacting the foregoing aldehyde with the foregoing anishydrazine at a substantially equal mol ratio in an appropriate organic solvent. However, taking the yield and the easiness of purification into consideration, it is preferable to use a stoichiometric excess amount of said anishydrazine. This reaction may be expedited by adding an acid as is generally known. As the acid catalyst for this purpose, mineral acids such as hydrochloric acid, diluted sulfuric acid, etc. and organic acids such as acetic acid are useful. As the reaction solvent, almost all organic solvents are useful as far as the materials employed can be dissolved satisfactorily. To enumerate applicable organic solvents, there are lower alcohols such as methanol, ethanol, etc., cyclic ethers such as 1,4-dioxane, tetrahydrofuran, etc., cellosolves such as methyl cellosolve, ethyl cellosolve, etc., N,N-dimethylformamide, acetic acid, and the like. The reaction temperature varies with the reaction solvent employed, but it is optionally selected in the range of from room temperature to the boiling point of these solvents. In the case where a solvent having a good solubility for the materials employed, such as N,N-dimethylformamide, is used as a reaction solvent, the reaction progresses at room temperature, but in the case where a solvent wherein the materials employed are hard to dissolve at room temperature, such as ethanol, it is preferable to heat said solvent while refluxing. In either case, the reaction is completed in 1 to 5 hours, and the thus separated crystals are filtered out, or, in the case where the products do not precipitate in the reaction mixture, the reaction mixture is diluted with a poor solvent to thereby separate precipitates, and said precipitates are filtered out and recrystallized from an appropriate solvent, whereby there is obtained a pure hydrazone compound expressed by the general formula I.

Hereunder given are examples of the novel hydrazone compounds expressed by the general formula I according to the present invention, which are to be obtained through the foregoing process.

| Structural formula | Compound No. |
|---|---|
| ![structure] | (1) |

Since the portion

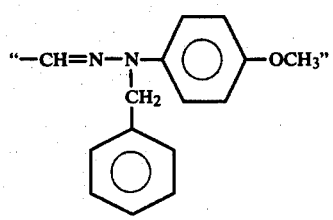
of the above formula is common to all the compounds below, it will be expressed by "Y" for short.
(2) 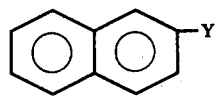
(3) 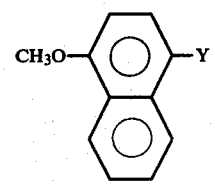
(4) 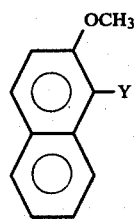
(5) 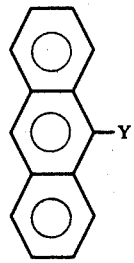
(6) 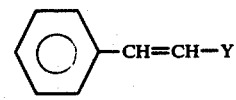
(7) 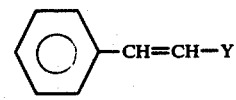
(8) 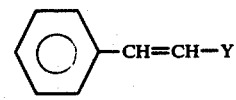
(9) 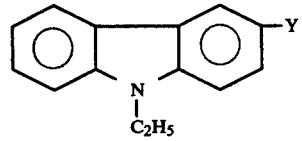
(10) 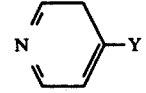
(11) 
(12) 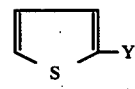
On the other hand, to give concrete examples of the hydrazone compounds expressed by the general formula II which are useful in the photosensitive elements of the present invention, the following compounds can be cited.
(13) 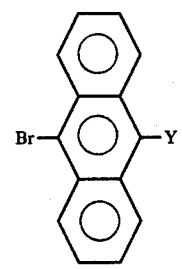
(14) 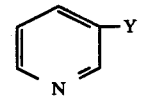
(15) 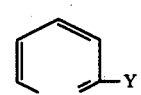
(16) 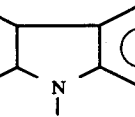
(17) 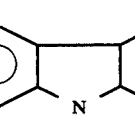
(18) 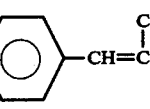

In this context, the hydrazone compounds (13) through (18) can be manufactured through the same process used for manufacturing the hydrazone compounds expressed by the general formula I.

Figure 1:
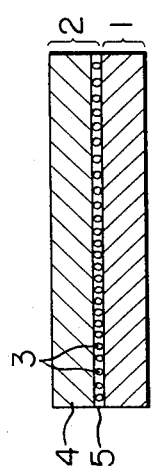
FIG. 1 is an enlarged cross-sectional view of an electrophotographic element according to the present invention.

In the drawings, 1 denotes an electrically conductive substrate, 2 denotes a photosensitive layer, 3 denotes a charge carrier generating material, 4 denotes a charge transfer layer, and 5 denotes a charge carrier generating layer.

Next, the photosensitive element according to the present invention will be explained with reference to the attached drawings. FIG. 1 of the drawings illustrates an example of the structure of an electrophotographic element according to the present invention. This element comprises an electrically conductive substrate 1, a charge carrier generating layer 5 consisting essentially of a charge carrier generating material and a charge transfer layer 4 containing a hydrazone compound expressed by the general formula II, said two layers being successively superposed on said substrate.

To work as a charge transfer material, the hydrazone compound expressed by the general formula II forms a charge transfer medium together with a binder (and a plasticizer as occasion demands), while a charge carrier generating material, such as inorganic or organic pigment, generates charge carriers. On this occasion, said charge transfer medium has an ability to accept mainly the charge carriers generated by the charge carrier generating material and to transfer said charge carriers. In this context, materials to be used in a photosensitive element should satisfy the fundamental requisite that the charge carrier generating material and the hydrazone compound expressed by the general formula II are mutually free from overlapping of their absorption wavelength region mainly in the visible region. The reason is that it is necessary to transmit light efficiently to the surface of the charge carrier generating material. The hydrazone compound expressed by the general formula II for use in the photosensitive element of the present invention has characteristics that it shows no substantial absorption of light in the visible region and works especially effectively as a charge transfer material when combined with a charge carrier generating material which generally absorbs light of the visible region and generates charge carriers.

In the case of the photosensitive element illustrated herein, light applied thereto passes through the charge transfer layer 4, reaches the charge carrier generating layer 5 and causes generation of charge carriers at the light-struck portions of said charge carrier generating layer, while the charge carriers thus generated are injected into the charge transfer layer 4 and are transported therethrough. Accordingly, this photosensitive element may be said to have a mechanism so designed that the generation of charge carriers required for light decay is performed by the charge carrier generating material and the transfer of charge carriers is performed by the charge transfer medium (wherein a hydrazone compound of the general formula II according to the present invention works mainly).

This photosensitive element can be prepared by the steps of depositing a charge carrier generating material onto an electrically conductive substrate through vacuum evaporation or by coating a dispersion of fine particles of a charge carrier generating material in a suitable solvent containing, if needed, a binder dissolved therein, onto said substrate, and coating and drying on the resulting layer a solution containing a hydrazone compound expressed by the general formula II and a binder after, if further needed, a surface-finishing or flim-thickness-controlling of said layer has been completed by means of, for instance, buffing, etc. The coating is carried out by conventional means such as doctor blade, wire bar and the like.

Referring to the thickness of the photosensitive layer, as for the thickness of the charge carrier generating layer, it is $5\mu$ or less, preferably in the range of from 0.01 to $0.5\mu$, and as for the thickness of the charge transfer layer, it is in the range of from about 3 to $50\mu$, preferably from 5 to $20\mu$. The appropriate percentage of the hydrazone compound expressed by the general formula II to be contained in the photosensitive layer is in the range of from 10 to 95% by weight, preferably from 30 to 90% by weight.

Further, it is to be noted that, in preparing the photosensitive element of the present invention as above, a plasticizer may be employed together with a binder.

As the electrically conductive substrate for use in the photosensitive element of the present invention, metal plates or metal foils of aluminum and the like, plastic films deposited with a metal such as aluminum and the like or electroconductive-processed papers, etc. are useful. As the binders suitable for use in the present invention, there can be enumerated condensation resins such as polyamide, polyurethane, polyester, epoxy resin, polyketone, polycarbonate, etc.; vinyl polymers such as polyvinylketone, polystyrene, poly-N-vinylcarbazole, polyacrylamide, acryl resins, polyvinylacetal, etc., and the like. However, it is to be understood that any insulating and adhesive resins may be employed in the present invention. As the plasticizers suitable for use in the present invention, there can be enumerated halogenized paraffin, polybiphenyl chloride, dimethylnaphthalene, dibutylphthalate, etc. As the charge carrier generating material suitable for use in the present invention, there can be enumerated inorganic pigment such as, for instance, selenium, seleniumtellurium alloy, cadmium sulfide, cadmium sulfide-selenium alloy, etc.; organic pigments such as, for instance, CI Pigment Blue 25 (Color Index CI 21180), CI Pigment Red 41 (CI 21200), CI Acid Red 52 (CI 45100), CI Basic Red 3 (CI 45210), disazo or trisazo pigments such as disazo pigment having carbazole skeleton (as disclosed in Japanese Laid-open Patent Application No. 95966/1978), disazo pigment having styrylstilbene skeleton (as disclosed in Japanese Laid-open Patent Application No. 13445/1978), triazo pigment having triphenylamine skeleton (as disclosed in Japanese Laid-open Patent Application No. 132347/1978), disazo pigment having dibenzothiophene skeleton (as disclosed in Japanese Laid-open Patent Application No. 21728/1980), disazo pigment having oxadiazole skeleton (as disclosed in Japanese Laid-open Patent Application No. 12742/1979), disazo pigment having fluorenone skeleton (as disclosed in Japanese Laid-open Patent Application No. 22834/1979), disazo pigment having stilbene skeleton (as disclosed in Japanese Laid-open Patent Application No. 20737/1979), disazo pigment having distyryloxadiazole skeleton (as disclosed in Japanese Laid-open Patent Application No. 2129/1979), disazo pigment having distyrylcarbazole skeleton (as disclosed in Japanese Laid-open Patent Application No. 14967/1979), etc.; phthalocyanine pigments such as, for instance, CI Pigment Blue 16 (CI 74100), etc.; indigo pigments such as, for instance, CI Bat Brown 5 (CI 73410), CI Bat Dye (CI 73030), etc.; and perylene pigments such as, for instance, Algoscarlet B (the manufacture of Bayer Co.), Indanthrene Scarlet B (the manufacture of Bayer Co.), etc.

Further, it is to be noted that in each of the photosensitive elements to be prepared as above, an adhesive layer or a barrier layer may be interposed between the electrically conductive substrate and the photosensitive layer as occasion demands. The appropriate materials for these layers include polyamide, nitrocellulose, aluminum oxide and the like, and the preferable thickness of said layers is 1μ or less.

The reproduction using the photosensitive element of the present invention is achieved by electrifying the surface of the photosensitive layer of the element, exposing the same to light, developing thereafter and, if needed, transferring to paper or the like.

The photosensitive element according to the present invention has excellent advantages such that it is generally high in sensitivity and is rich in flexibility.

DESCRIPTION OF THE PREFERRED EMBODIMENTS

Example 1

Preparation of Compound (1) 1.56 gr (0.01 mol) of 1-naphthylaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate-ethanol, whereby there were obtained 2.88 gr of the intended hydrazone compound (1). The yield was 78.7% and the melting point of the product was in the range of from 157.0° to 157.5° C. The results of the elementary analysis of this compound were as shown below.

|       | Measured value | Calculated value |
|-------|----------------|------------------|
| C (%) | 81.90          | 81.94            |
| H (%) | 6.01           | 6.05             |
| N (%) | 7.56           | 7.65             |

Figure 2:
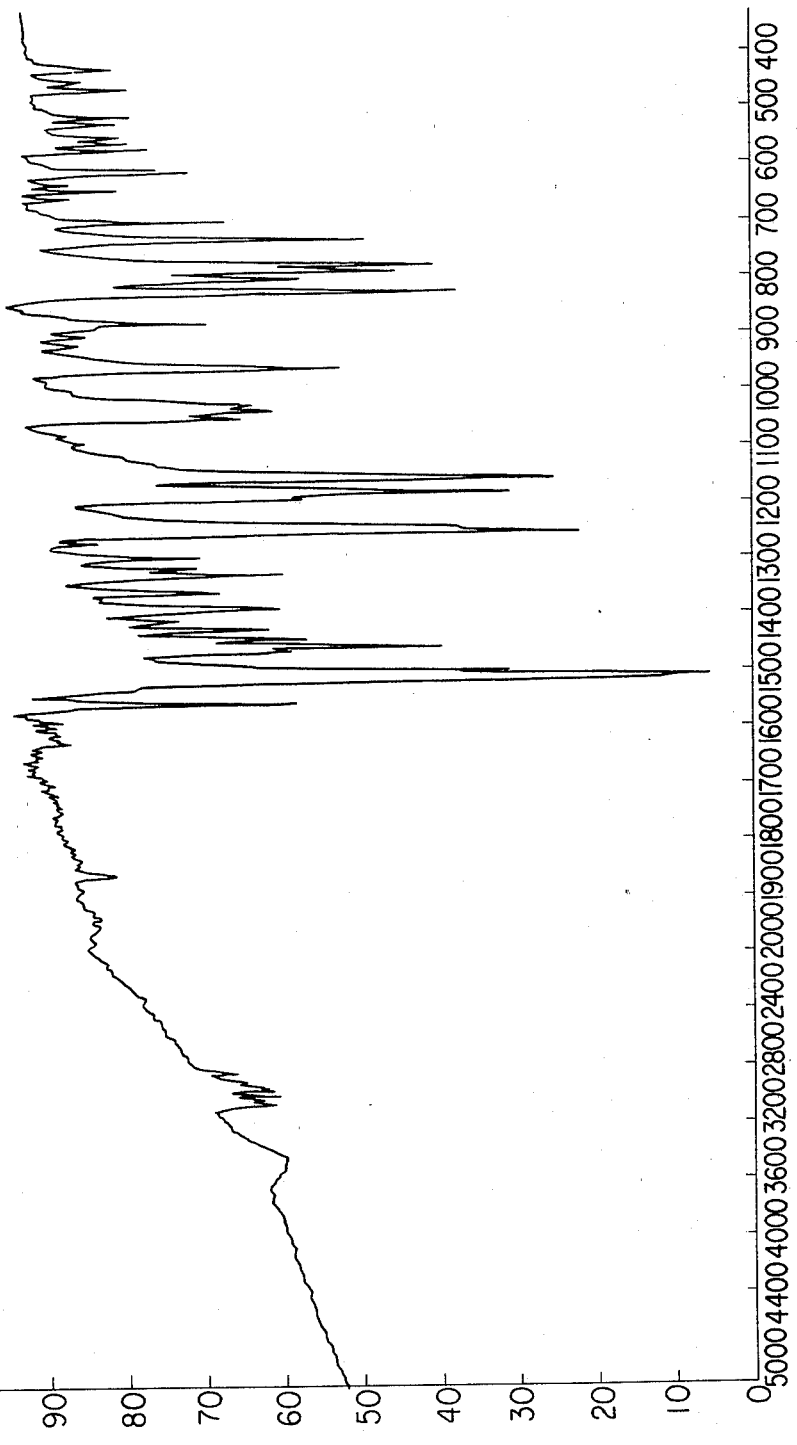
FIGS. 2 through 13 illustrate infrared absorption spectra of the respective hydrazone compounds of the present invention prepared in Examples 1 through 12.

The infrared absorption spectrum (taken by KBr tablet method) of this compound was as shown in FIG. 2.

Example 2

Preparation of Compound (2)

1.56 gr (0.01 mol) of 2-naphthylaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate, whereby there were obtained 3.15 gr of the intended hydrazone compound (2). The yield was 86.1% and the melting point of the product was in the range of from 178.5° to 179.0° C. The results of the elementary analysis of this compound were as shown below.

|       | Measured value | Calculated value |
|-------|----------------|------------------|
| C (%) | 81.88          | 81.94            |
| H (%) | 5.97           | 6.05             |
| N (%) | 7.53           | 7.65             |

Figure 3:
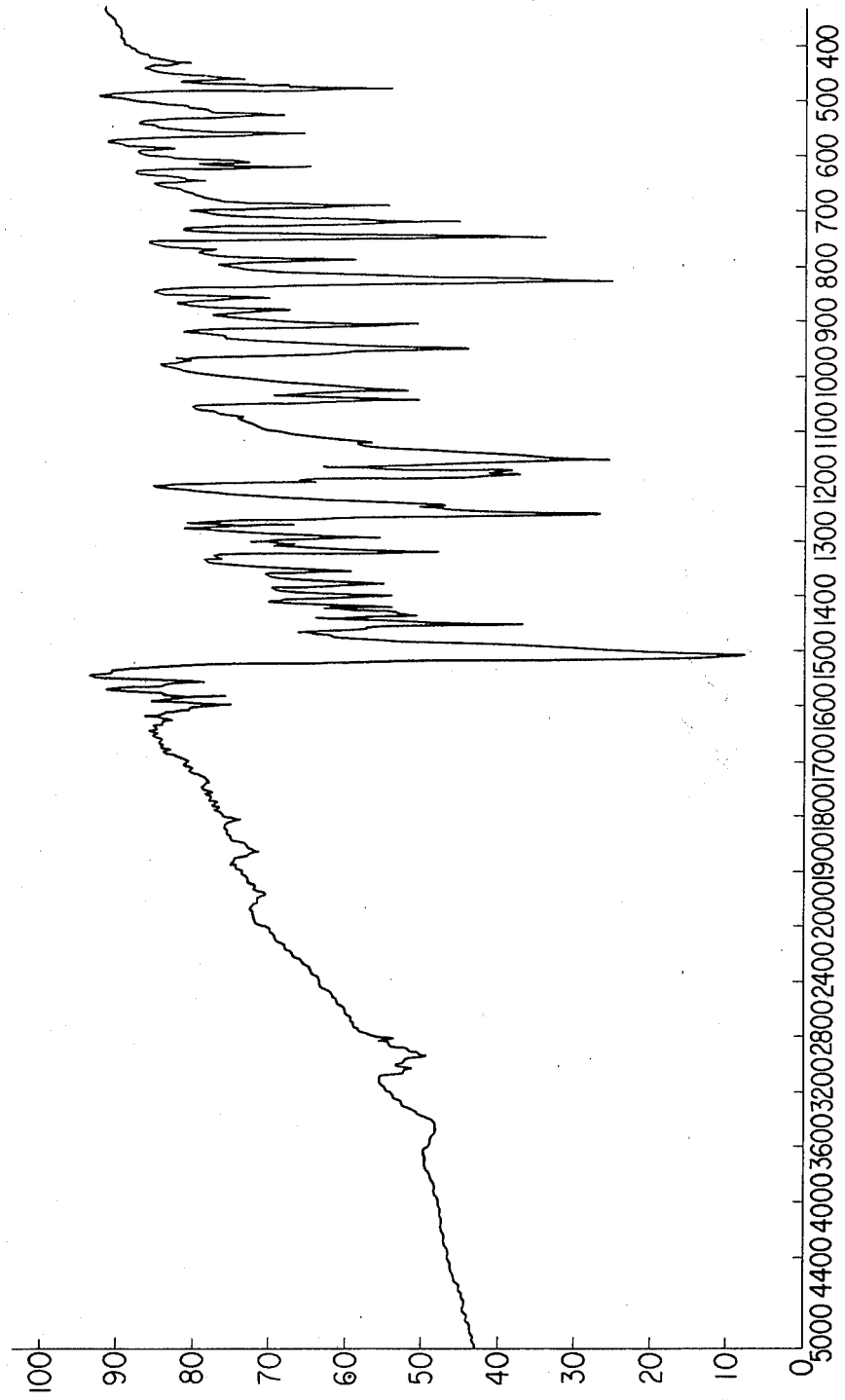

The infrared absorption spectrum (taken by KBr tablet method; the same applies hereinafter) of this compound was as shown in FIG. 3.

Example 3

Preparation of Compound (3)

1.86 gr (0.01 mol) of 4-methoxy-1-naphthylaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate-ethanol, whereby there were obtained 3.21 gr of the intended hydrazone compound (3). The yield was 81.1% and the melting point of the product was in the range of from 107.5° to 108.5° C. The results of the elementary analysis of this compound were as shown below.

|       | Measured value | Calculated value |
|-------|----------------|------------------|
| C (%) | 78.62          | 78.76            |
| H (%) | 6.04           | 6.10             |
| N (%) | 6.94           | 7.07             |

Figure 4:
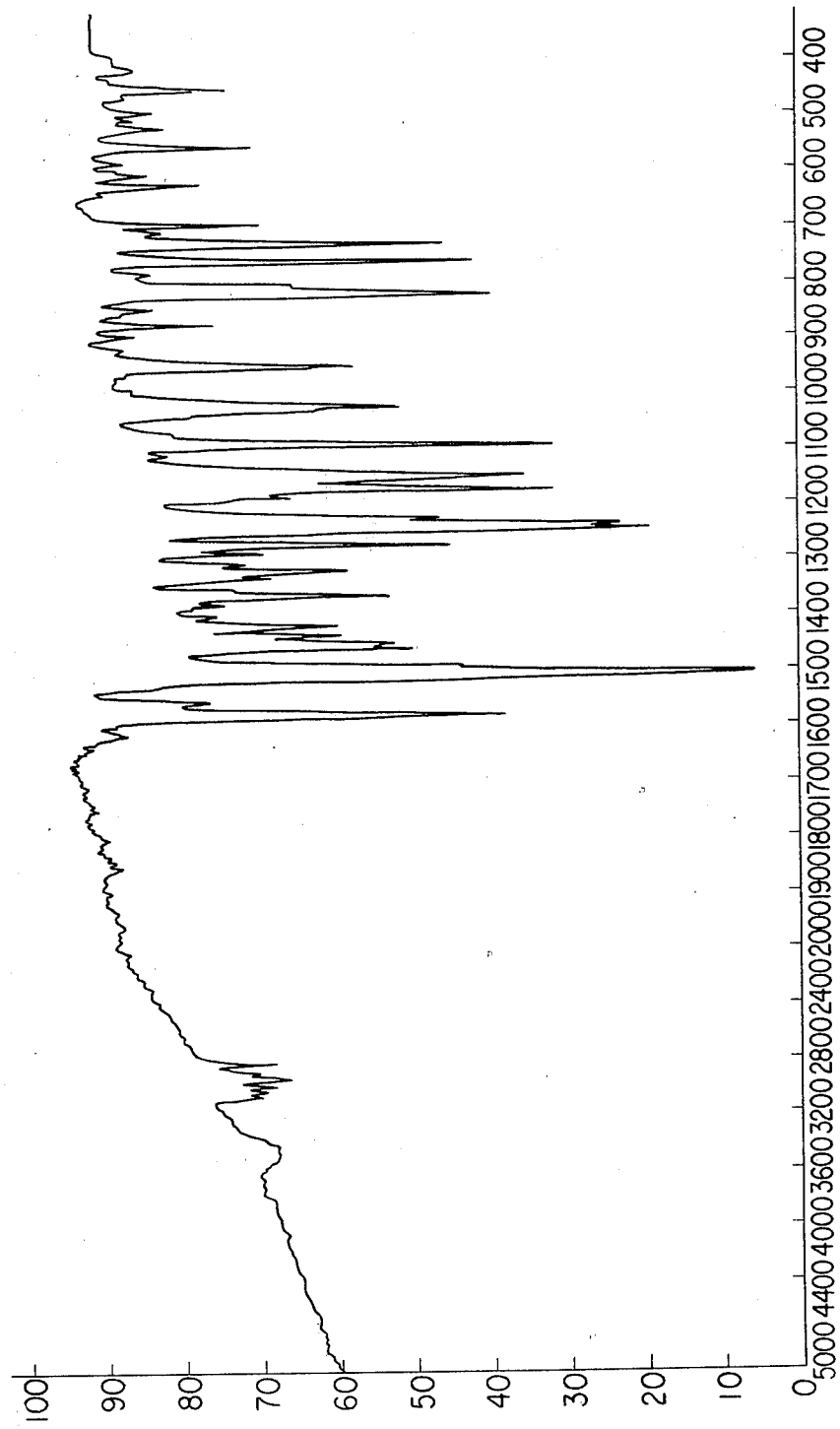

The infrared absorption spectrum of this compound was as shown in FIG. 4.

Example 4

Preparation of Compound (4)

1.86 gr (0.01 mol) of 2-methoxy-1-naphthylaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate-ethanol, whereby there were obtained 3.40 gr of the intended hydrazone compound (4). The yield was 85.9% and the melting point of the product was in the range of from 104.0° to 105.0° C. The results of the elementary analysis of this compound were as shown below.

|       | Measured value | Calculated value |
|-------|----------------|------------------|
| C (%) | 78.68          | 78.76            |
| H (%) | 6.02           | 6.10             |
| N (%) | 6.92           | 7.07             |

Figure 5:
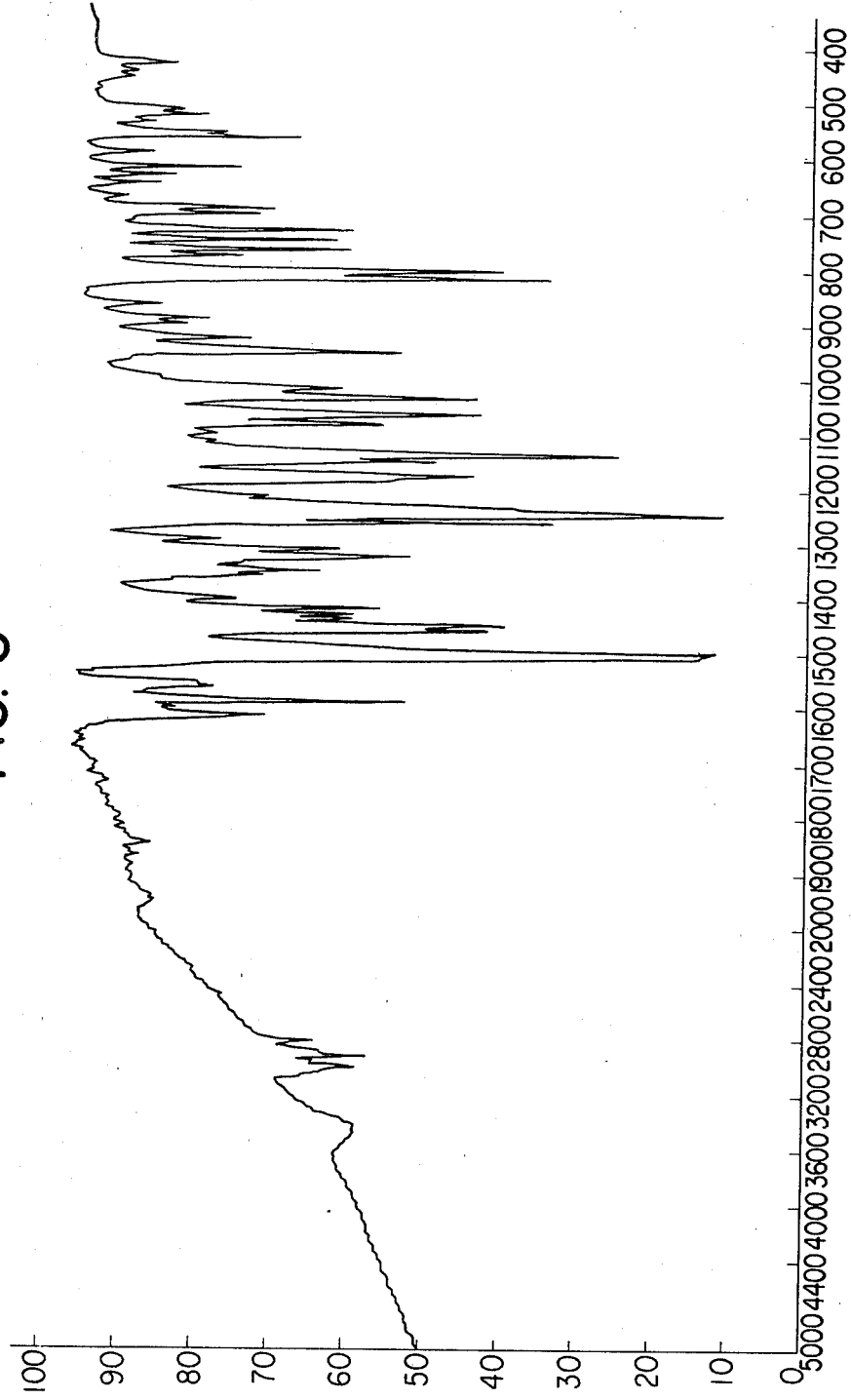

The infrared absorption spectrum of this compound was as shown in FIG. 5.

Example 5

Preparation of Compound (5)

2.06 gr (0.01 mol) of 9-formylanthracene and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate, whereby there were obtained 3.19 gr of the intended hydrazone compound (5). The yield was 76.7% and the melting point of the product was in the range of from 185.5° to 186.0° C. The results of the elementary analysis of this compound were as shown below.

|       | Measured value | Calculated value |
|-------|----------------|------------------|
| C (%) | 83.95          | 83.63            |
| H (%) | 5.80           | 5.80             |
| N (%) | 7.10           | 6.73             |

Figure 6:
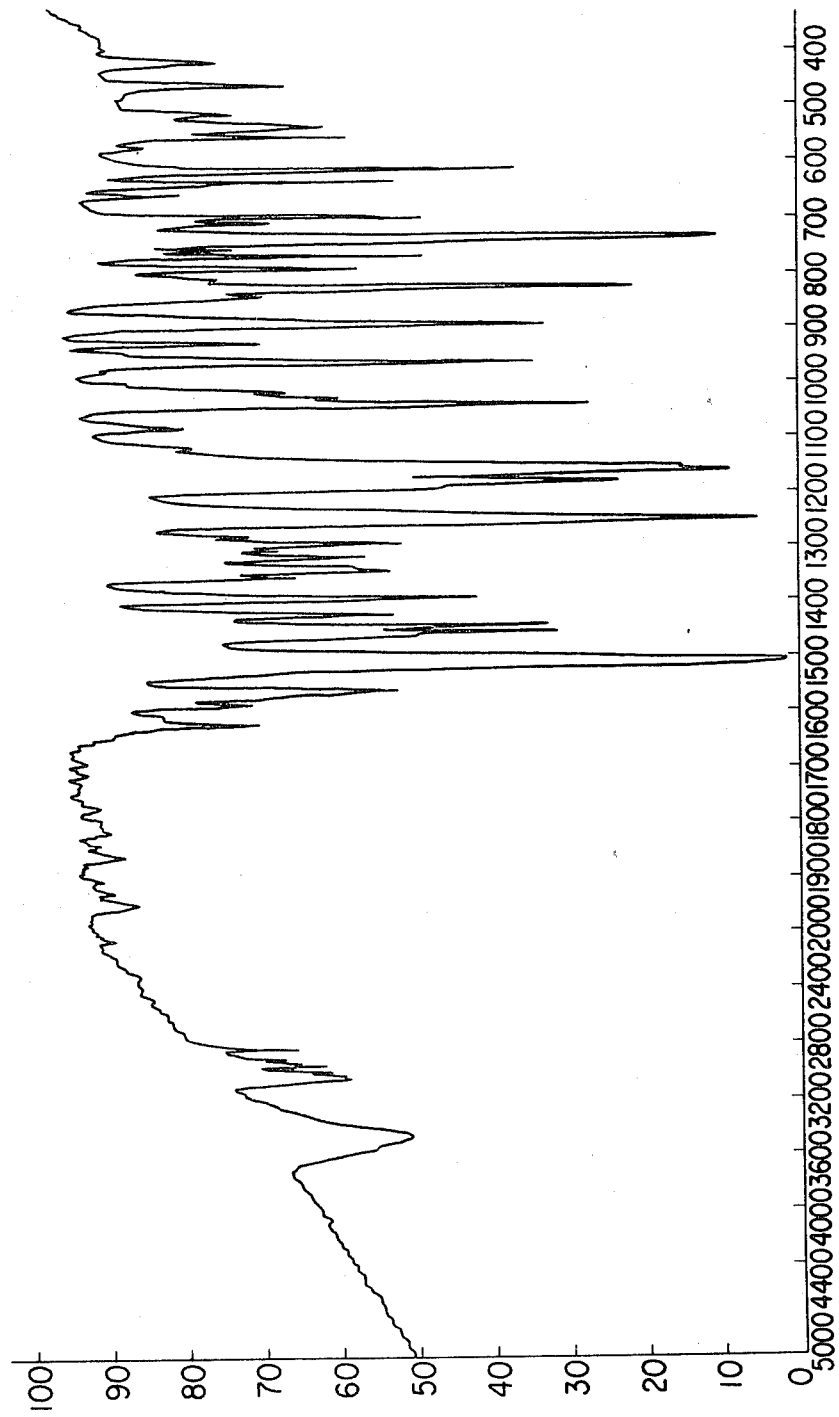

The infrared absorption spectrum of this compound was as shown in FIG. 6.

Example 6

Preparation of Compound (6)

1.32 gr (0.01 mol) of transcinnamaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate, whereby there were obtained 2.82 gr of the intended hydrazone compound (6). The yield was 82.5% and the melting point of the product was in the range of from 153.5° to 155.0° C. The results of the elementary analysis of this compound were as shown below.

|       | Measured value | Calculated value |
|-------|----------------|------------------|
| C (%) | 80.60          | 80.67            |
| H (%) | 6.50           | 6.48             |
| N (%) | 8.00           | 8.18             |

Figure 7:
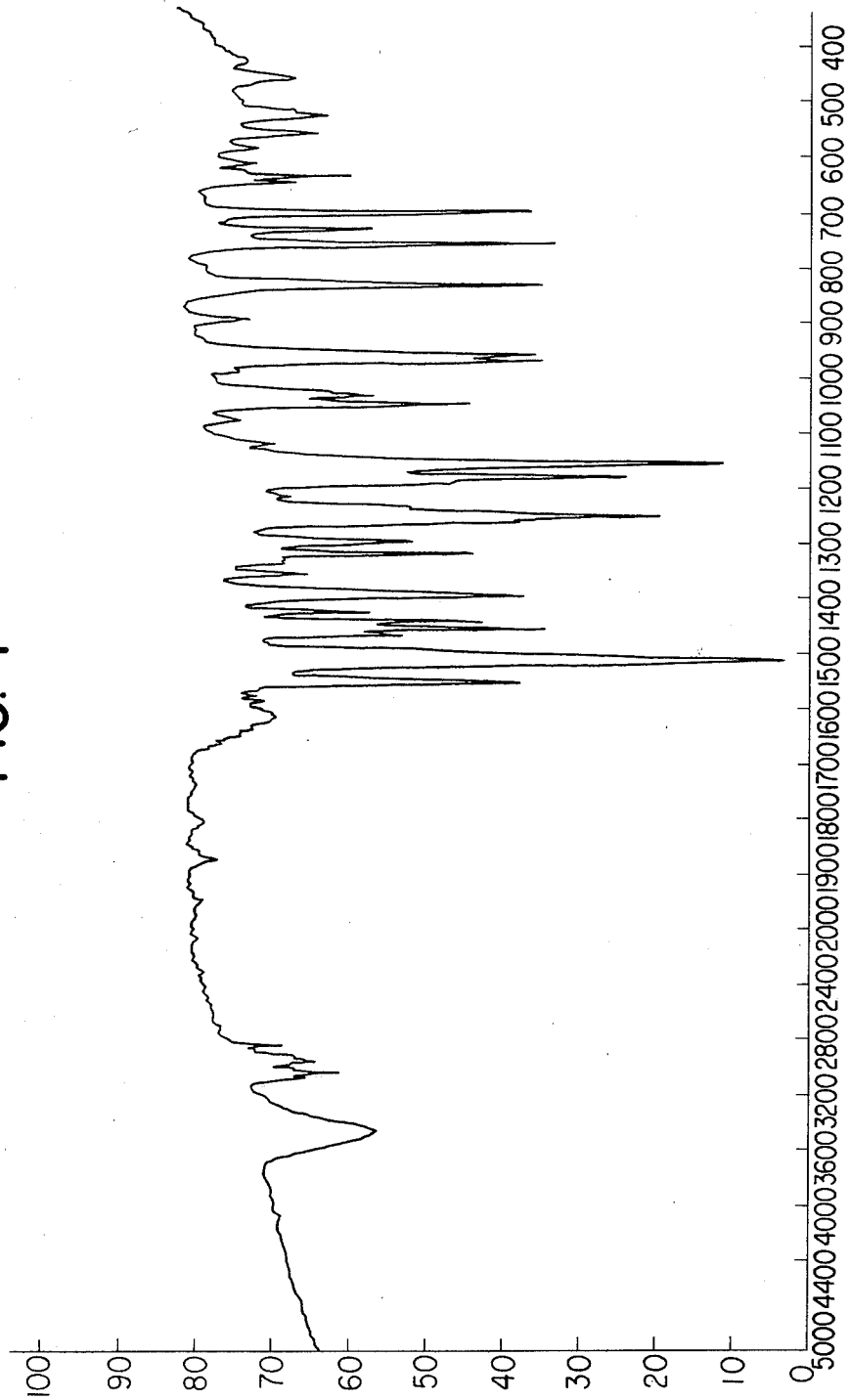

The infrared absorption spectrum of this compound was as shown in FIG. 7.

Example 7

Preparation of Compound (7)

1.75 gr (0.01 mol) of 4-(N,N-dimethylamino)transcinnamaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate-ethanol, whereby there was obtained 2.90 gr of the intended hydrazone compound (7). The yield was 75.3% and the melting point of the product was in the range of from 158.5° to 159.0° C. The results of the elementary analysis of this compound were as shown below.

|       | Measured value | Calculated value |
|-------|----------------|------------------|
| C (%) | 78.30          | 77.89            |
| N (%) | 7.10           | 7.06             |
| H (%) | 10.90          | 10.90            |

Figure 8:
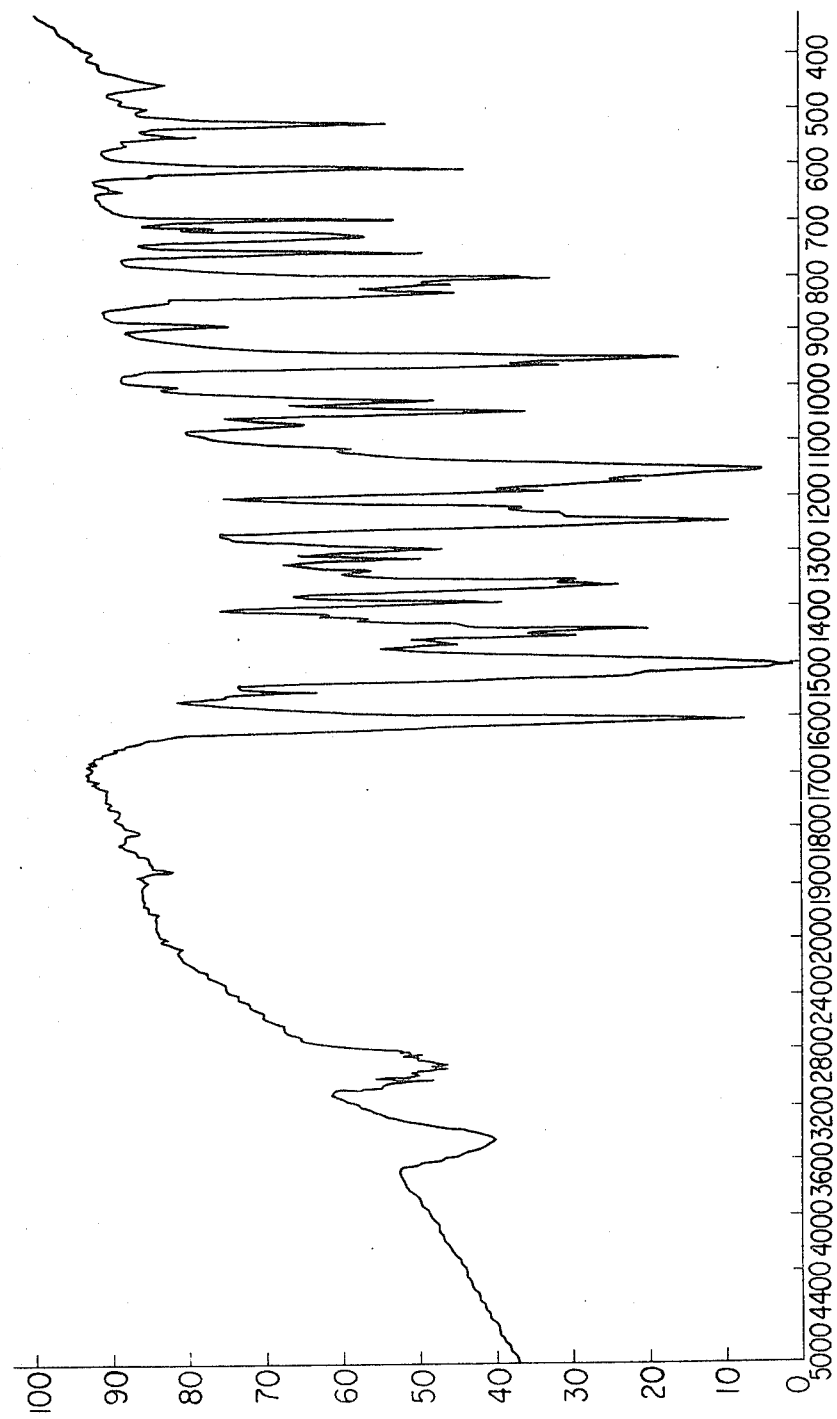

The infrared absorption spectrum of this compound was as shown in FIG. 8.

Example 8

Preparation of Compound (8)

1.62 gr (0.01 mol) of 2-methoxytranscinnamaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethanol, whereby there were obtained 2.91 gr of the intended hydrazone compound (8). The yield was 78.2% and the melting point of the product was in the range of from 118.0° to 119.5° C. The results of the elementary analysis of this compound were as shown below.

|       | Measured value | Calculated value |
|-------|----------------|------------------|
| C (%) | 77.20          | 77.39            |
| H (%) | 6.10           | 6.50             |
| N (%) | 7.50           | 7.52             |

Figure 9:
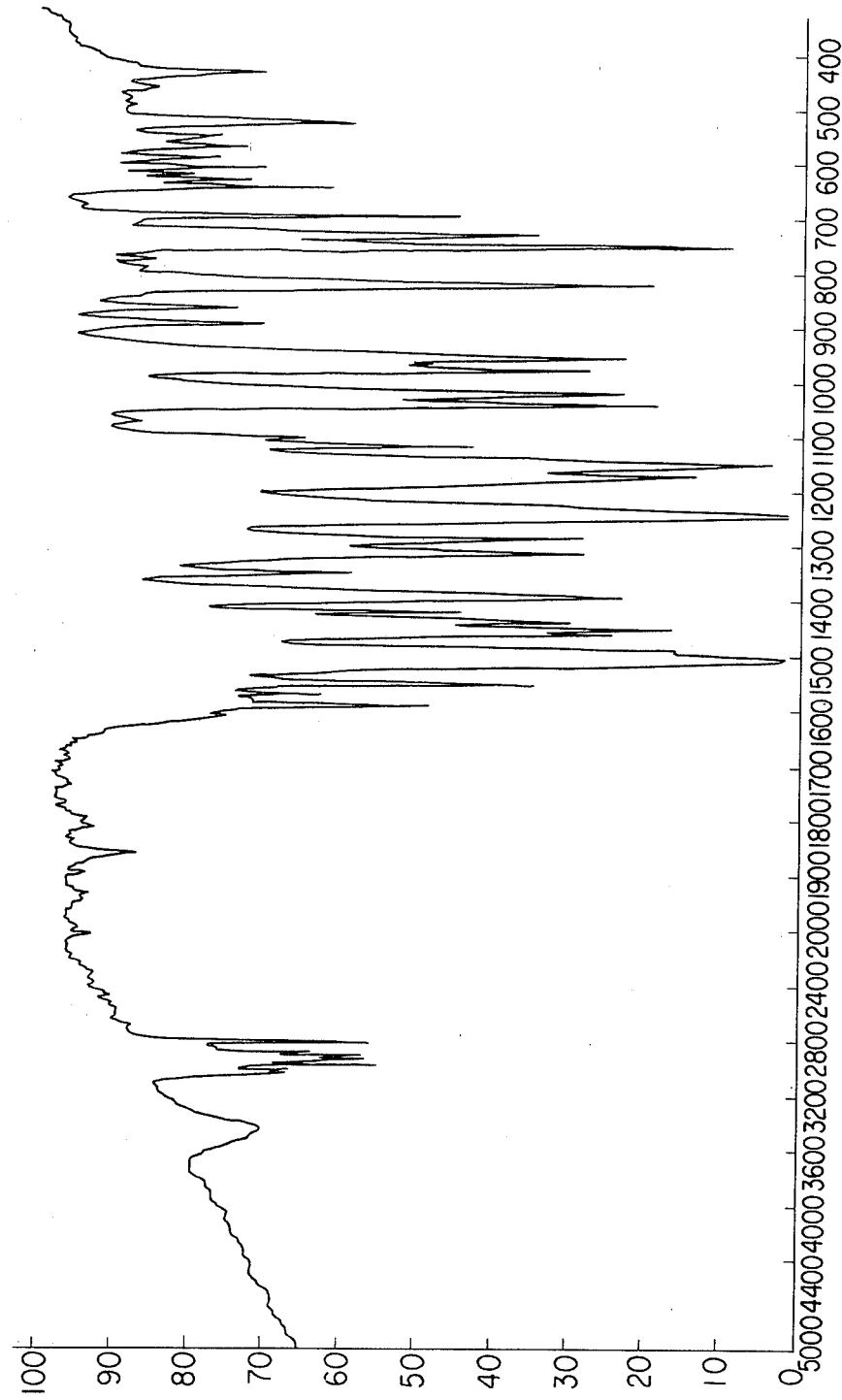

The infrared absorption spectrum of this compound was as shown in FIG. 9.

Example 9

Preparation of Compound (9)

2.23 gr (0.01 mol) of 9-ethylcarbazole-3-aldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate, whereby there were obtained 3.64 gr of the intended hydrazone compound (9). The yield was 84.1% and the melting point of the product was in the range of from 189.5° to 190.5° C. The results of the elementary analysis of this compound were as shown below.

|       | Measured value | Calculated value |
|-------|----------------|------------------|
| C (%) | 80.30          | 80.34            |
| H (%) | 5.80           | 6.28             |
| N (%) | 9.60           | 9.69             |

Figure 10:
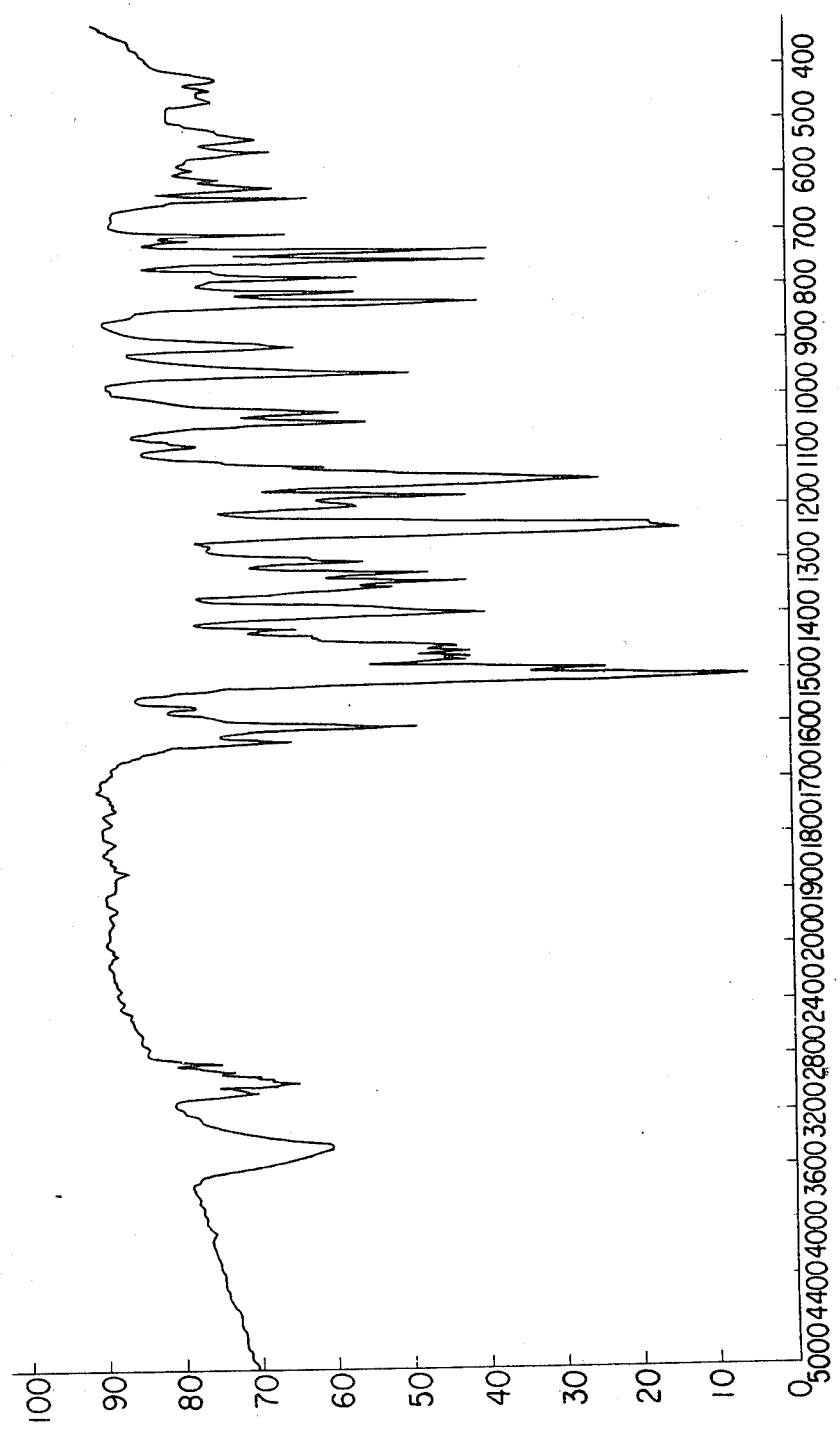

The infrared absorption spectrum of this compound was as shown in FIG. 10.

Example 10

Preparation of Compound (10)

1.07 gr (0.01 mol) of 3-pyridylaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from cyclohexane, whereby there were obtained 2.18 gr of the intended hydrazone compound (10). The yield was 68.8% and the melting point of the product was in the range of from 114.0° to 115.0° C. The results of the elementary analysis of this compound were as shown below.

|       | Measured value | Calculated value |
|-------|----------------|------------------|
| C (%) | 76.19          | 75.68            |
| H (%) | 6.01           | 6.03             |
| N (%) | 13.22          | 13.24            |

Figure 11:
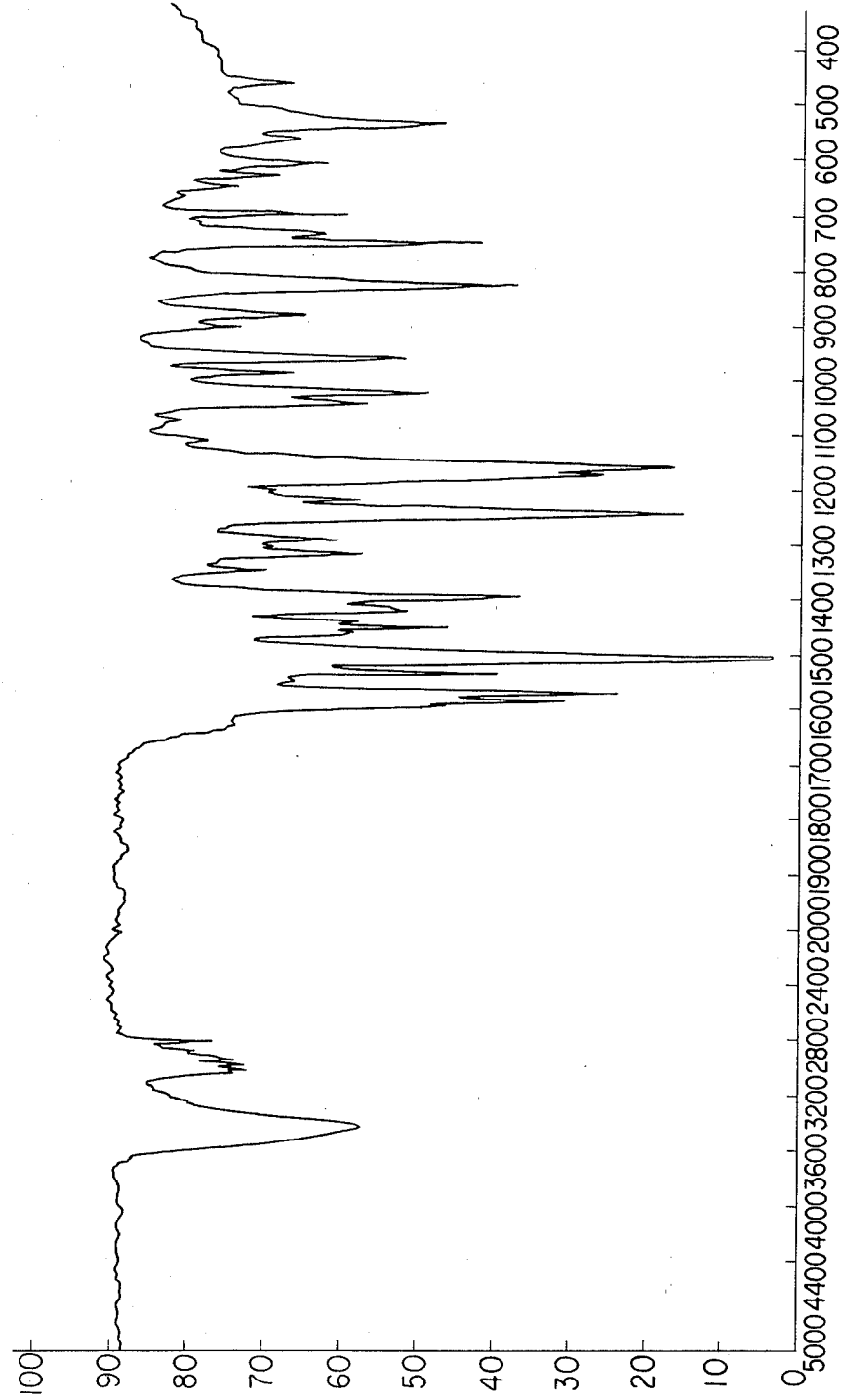

The infrared absorption spectrum of this compound was as shown in FIG. 11.

Example 11

Preparation of Compound (11)

0.96 gr (0.01 mol) of furfural and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating out refluxing. After letting the mixture cool, the separated crystals were filtered out, dried and recrystallized from ethanol, whereby there were obtained 2.43 gr of the intended hydrazone compound (11). The yield was 79.4% and the melting point of the product was in the range of from 128.0° to 129.0° C. The results of the elementary analysis of this compound were as shown below.

|       | Measured value | Calculated value |
|-------|----------------|------------------|
| C (%) | 74.55          | 74.49            |
| H (%) | 5.91           | 5.92             |
| N (%) | 9.11           | 9.15             |

Figure 12:
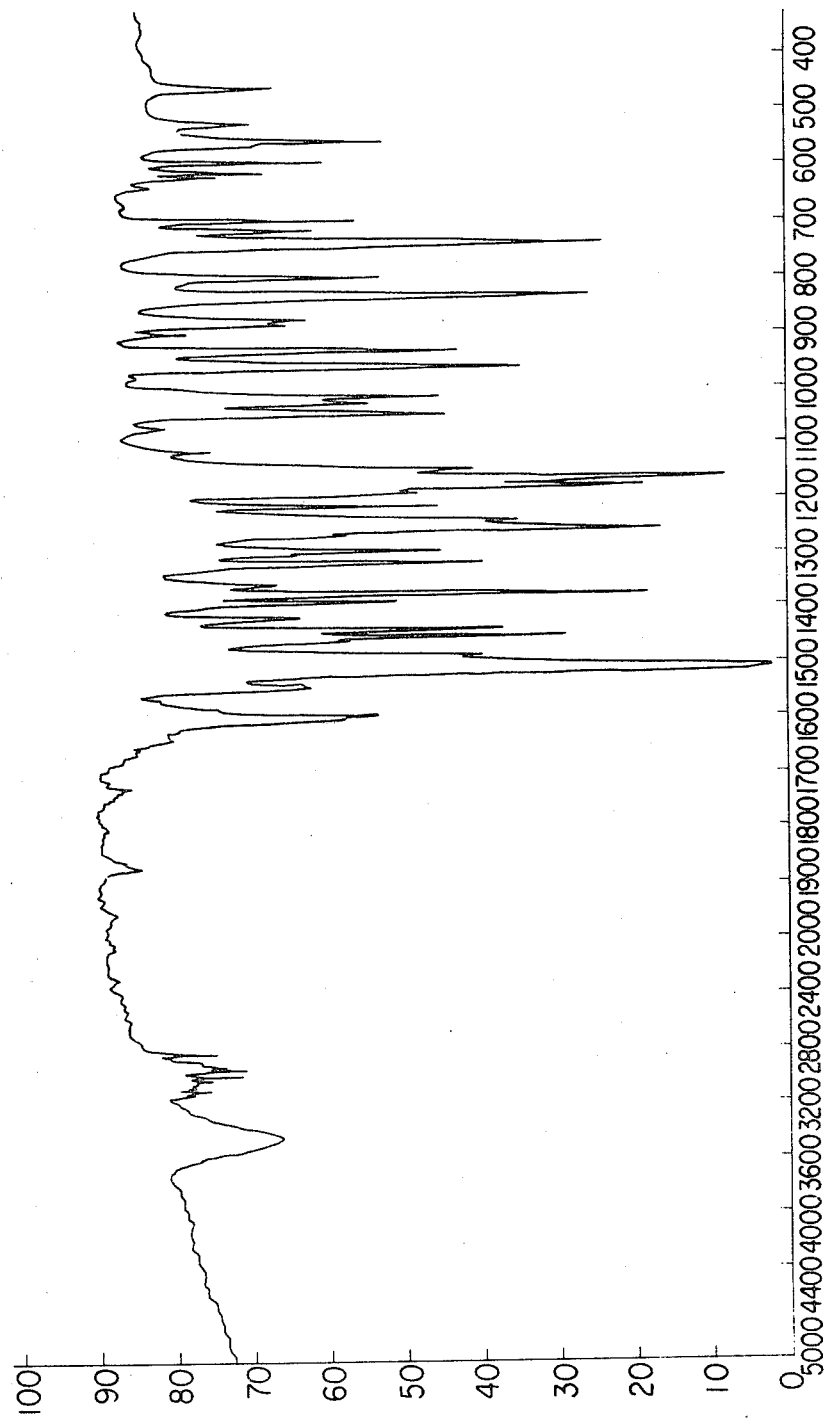

The infrared absorption spectrum of this compound was as shown in FIG. 12.

Example 12

Preparation of Compound (12)

1.30 gr (0.012 mol) of 2-thienylaldehyde and 3.42 gr (0.015 mol) of 1-benzyl-1-p-anishydrazine were added to 50 ml of ethanol. Then, after further adding several drops of 1 N hydrochloric acid, the resulting mixture was subjected to 1 hour's stirring while heating and refluxing. After letting the mixture cool, the separated crystals were filtered out, dried and recrystallized from ethyl acetate-ethanol, whereby there were obtained 2.48 gr of the intended hydrazone compound (12.) The yield was 66.3% and the melting point of the product was in the range of from 118.0° to 119.0° C. The results of the elementary analysis of this compound were as shown below.

|       | Measured value | Calculated value |
|-------|----------------|------------------|
| C (%) | 70.68          | 70.78            |
| H (%) | 5.58           | 5.63             |
| N (%) | 8.58           | 8.69             |

Figure 13:
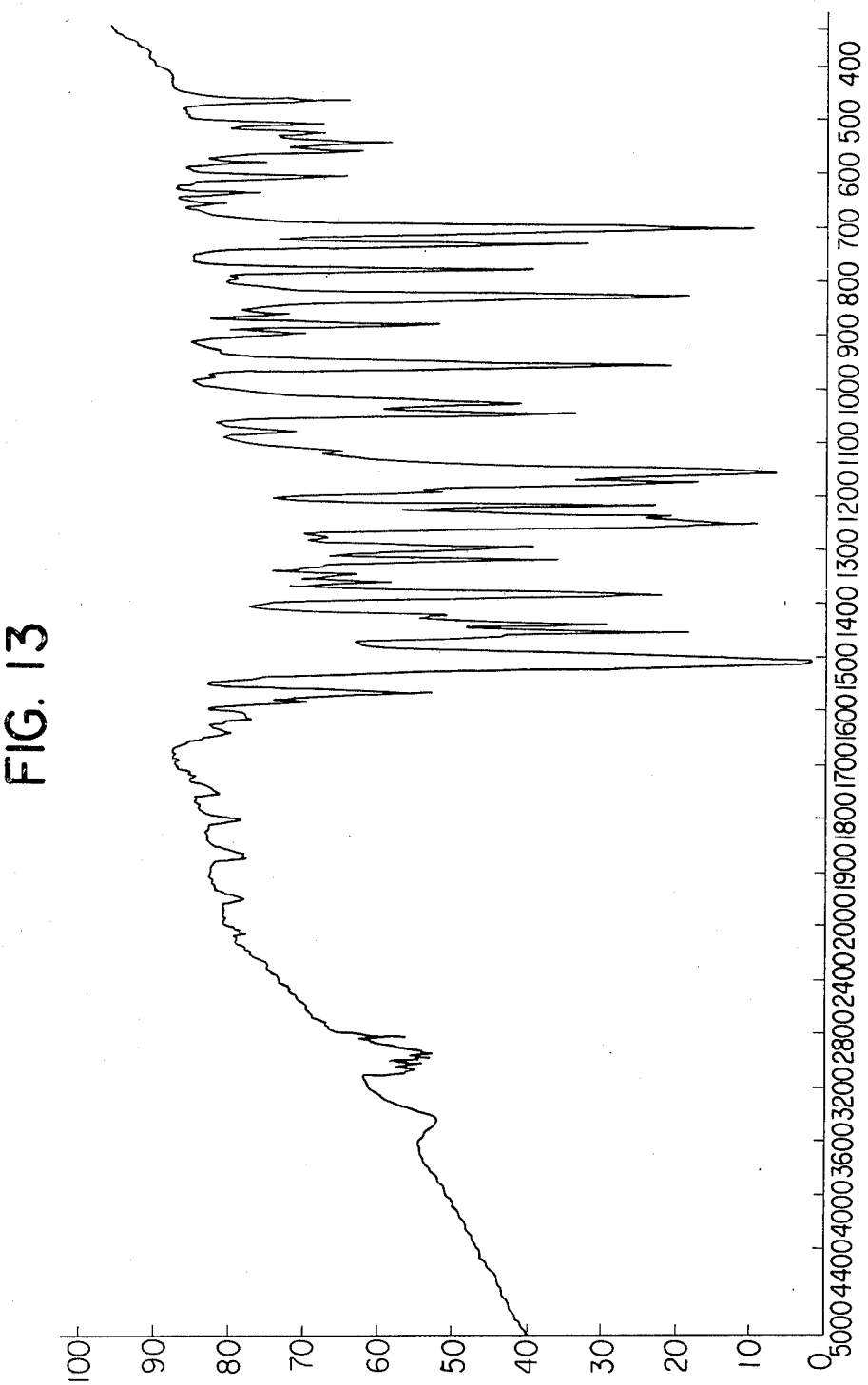

The infrared absorption spectrum of this compound was as shown in FIG. 13.

Example 13

2 parts ("part" herein means "part by weight"; the same applies hereinafter) of Dian Blue (CI 21180) and 98 parts of tetrahydrofuran were pulverized and mixed in a ball mill to thereby obtain a charge carrier generating pigment dispersion. The dispersion was coated onto a polyester film deposited with aluminum through vacuum evaporation (hereinafter called "aluminized polyester film" for short) by means of a doctor blade and was air-dried to thereby form a 0.5μ-thick charge carrier generating layer. Next, a charge transfer layer forming liquid obtained by mixing and dissolving 2 parts of the hydrazone compound (2) and 3 parts of polycarbonate resin in 45 parts of tetrahydrofuran was coated onto the foregoing charge carrier generating layer by means of a doctor blade and was dried at 100° C. for 10 minutes to form an about 10μ-thick charge transfer layer, whereby a photosensitive element was prepared.

This photosensitive element was subjected to $-6$ KV corona discharge for 20 seconds by means of an electrostatic copying paper analyzer tester (SP 428 type, the manufacture of K. K. KAWAGUCHI DENKI SEISAKUSHO) to charge negatively. Thereafter, the same was left standing in the dark for 20 seconds to thereby measure the surface potential Vpo (volt) at that time. Subsequently, the element was exposed to radiation of light from a tungsten lamp so as to attain the surface intensity of illumination of 20 luxes. Then, the time (second) required until the surface potential was reduced to ½ of said Vpo was measured and the amount of light-exposure E½ (lux.sec.) was calculated. The results thus obtained showed that Vpo was $-550$ volts and E½ was 7.5 lux.sec.

Example 14

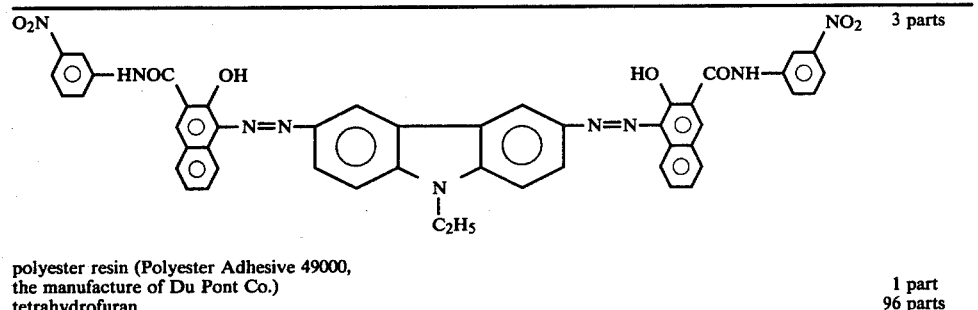

polyester resin (Polyester Adhesive 49000, the manufacture of Du Pont Co.)    1 part
tetrahydrofuran    96 parts A liquid having the above composition was pulverized and mixed in a ball mill, whereby a charge carrier generating pigment dispersion was obtained. This dispersion was coated onto an aluminized polyester film by means of a doctor blade and was dried in a drier at 80° C. for 5 minutes to thereby form a 1μ-thick charge carrier generating layer. Next, a charge transfer layer forming liquid obtained by mixing and dissolving 2 parts of the hydrazone compound (3) and 3 parts of polycarbonate resin in 45 parts of tetrahydrofuran (Panlite L) was coated onto the foregoing charge carrier generating layer by means of a doctor blade and was dried at 100° C. for 10 minutes to form an about 10μ-thick charge transfer layer, whereby a photosensitive element according to the present invention was prepared. When this photosensitive element was negatively charged in the same way as in Example 13 and Vpo and E½ were measured, the results were as follows:

Vpo=−850 volts, E½=4.5 lux.sec.

Examples 15 and 16

When photosensitive elements were prepared through the same procedure as in Example 14 with the exception that the charge carrier generating pigment and the charge transfer material were changed respectively, the results of measurement of the values of Vpo and E½ were as shown in the following Table-1.

ferred onto a slick paper and fixed, whereby there was obtained a clear-cut image, respectively. In the case where a wet developer was employed as developer, there was also obtained a clear-cut image.

Example 17

A charge carrier generating layer was formed by depositing selenium to the extent of 1μ in thickness through vacuum evaporation on an aluminum plate of about 300μ in thickness. Next, a charge transfer layer forming liquid prepared by mixing and dissolving 2 parts of the hydrazone compound (18) and 3 parts of polyester resin (Polyester Adhesive 49000, the manufacture of Du Pont Co.) in 45 parts of tetrahydrofuran was coated onto the foregoing charge carrier generating layer (selenium deposited layer) by means of a doctor blade, air-dried, and thereafter dried under reduced pressure to form an about 10μ-thick charge transfer layer, whereby a photosensitive element according to the present invention was prepared. When this photosensitive element was subjected to the measurement of the values of Vpo and E½ in the same way as in Example 13, the results were as follows:

Vpo=−890 volts, E½=3.5 lux.sec.

Example 18

TABLE 1

| Example | Charge carrier generating pigment | Charge transfer material | Vpo (volt) | E1/2 (lux-sec) |
|---|---|---|---|---|
| 15 | 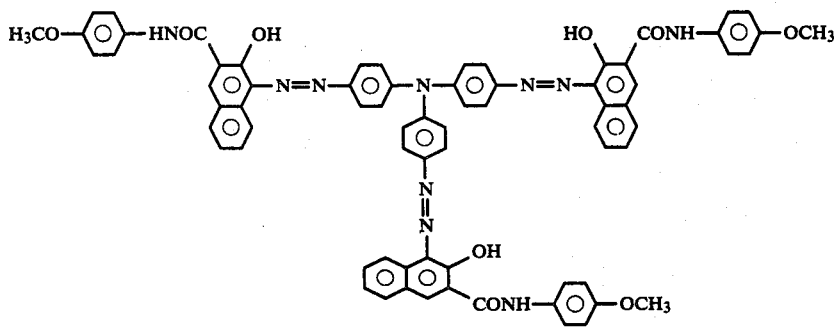 | (12) | 450 | 9.5 |
| 16 | 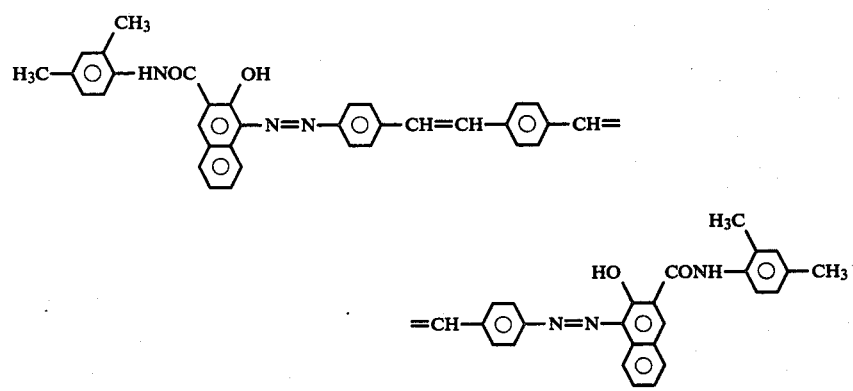 | (8) | 1304 | 1.9 |

Next, the photosensitive elements prepared in Examples 13 through 16 were negatively charged by means of the copying apparatus used in Example 13, exposed to radiation of light through an original to form an electrostatic latent image, and developed by means of a dry developer comprising a positively charged toner. Then, the thus developed image was electrostatically trans- By applying the same procedure as in Example 17 with the exception that a perylene pigment expressed by the following structural formula was deposited, in place of selenium employed in Example 17, through vacuum evaporation to the extent of about 0.3μ in thickness, a charge carrier generating layer was formed.

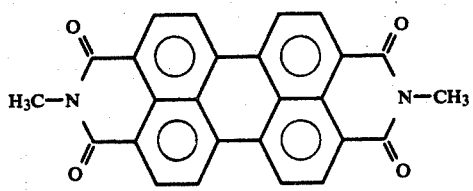

Subsequently, by applying the same procedure as in Example 17 with the exception that the charge transfer material employed therein was replaced by the hydrazone compound (10), a photosensitive element was prepared. When this photosensitive element was subjected to the measurement of the values of Vpo and E½ in the same way as in Example 17, the results were as follows:

Vpo = −730 volts, E½ = 9.0 lux.sec.

Next, the photosensitive elements prepared in Example 17 and 18 were negatively charged by means of the copying apparatus used in Example 13, exposed to radiation of light through an original to form an electrostatic latent image, and developed by means of a dry developer comprising a positively charged toner. Then, the thus developed image was electrostatically transferred onto a slick paper and was fixed, whereby there was obtained a clear-cut image, respectively. In the case where a wet developer was employed as developer, there was also obtained a clear-cut image.

Example 19

A mixture obtained by adding 158 parts of tetrahydrofuran to 1 part of Chlorodian Blue was pulverized and mixed in a ball mill. Thereafter, 12 parts of the hydrazone compound (9) and 18 parts of polyester resin (Polyester Adhesive 49000, the manufacture of Du Pont Co.) were added to the mixture and further mixed therewith, whereby a photosensitive layer forming liquid was prepared. By coating this liquid onto an aluminized polyester film by means of a doctor blade and was dried at 100° C. for 30 minutes to form an about 16 μ-thick photosensitive layer, whereby a photosensitive element according to the present invention was prepared.

When this photosensitive element was subjected to +6 KV corona discharge by means of the same apparatus as used in Example 13 to charge positively and the values of Vpo and E½ were measured, the results were as follows:

Vpo = 960 volts, E½ = 9.8 lux.sec.

Examples 20 to 22

A variety of photosensitive elements were prepared by repeating the same process for preparation of photosensitive element as in Example 19 with the exception that the charge carrier generating pigment and the charge transfer material used in Example 19 were replaced by ones shown in the following Table-2. Subsequently, the respective photosensitive elements were subjected to the same measurements as in Example 13, thereby obtaining the results shown in Table-2.

TABLE 2

| Example | Charge carrier generating pigment | Charge transfer material | Vpo (volt) | E½ (lux.sec) |
|---|---|---|---|---|
| 20 | [structure] | (1) | 1010 | 6.8 |
| 21 | [structure] | (11) | 620 | 10.3 |
| 22 | [structure] | (6) | 1210 | 10.5 |

Next, the photosensitive elements prepared in Examples 19 through 22 were positively charged by means of the same copying apparatus as used in Example 13, exposed to radiation of light through an original to form an electrostatic latent image, and developed by means of a dry developer comprising a negatively charged toner. Then, the thus developed image was electrostatically transferred onto a slick paper and was fixed, whereby there was obtained a clear-cut image. In the case where a wet developer was employed as developer, there was also obtained a clear-cut image.

Example 23

3 parts of the same charge carrier generating pigment as that employed in Example 16, 1 part of polyester resin (Polyester Adhesive 49000, the manufacture of Du Pont Co.) and 96 parts of tetrahydrofuran were pulverized and mixed in a ball mill. The resulting dispersion was coated onto an aluminized polyester film by means of a doctor blade and was dried in a drier at 80° C. for 5 minutes to thereby form an about 0.1 μ-thick charge carrier generating layer. Next, a solution consisting of 1 part of the hydrazone compound (3), 1 part of polycarbonate resin and 8 parts of tetrahydrofuran was coated onto the foregoing charge carrier generating layer by means of a doctor blade and was dried at 100° C. for 10 minutes to form an about 20 μ-thick charge transfer layer, whereby there was obtained a photosensitive element.

When this photosensitive element was charged negatively and subjected to the measurement of the values of Vpo and E½ in the same way as in Example 13, the results were as follows:

Vpo = −1339 volts, E½ = 2.1 lux.sec.

What is claimed is:

1. An electrophotographic element which comprises an electrically conductive substrate, and a charge carrier generating layer and a charge transfer layer superposed on said substrate, said charge transfer layer containing at least one hydrazone compound having the general formula:

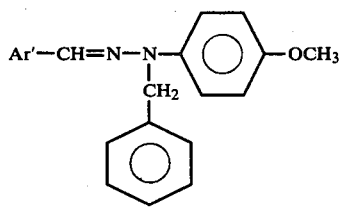

wherein Ar' is selected from the group consisting of styryl, α-methyl styryl, methoxy-substituted styryl and dimethylamino-substituted styryl; and a binder.

2. An electrophotographic element according to claim 1, wherein said hydrazone compound is selected from the group consisting of:

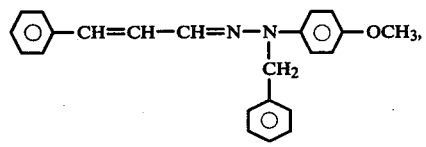

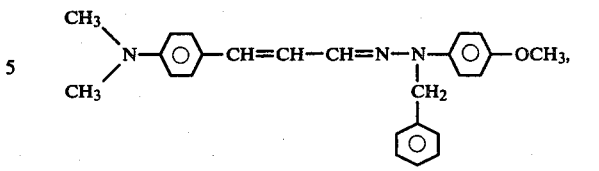

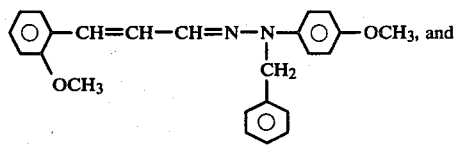

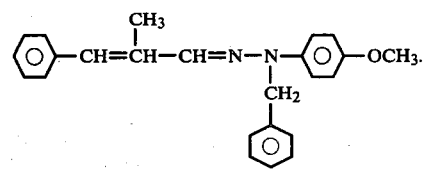

3. An electrophotographic element according to claim 1, wherein said charge carrier generating layer is interposed between said electrically conductive substrate and said charge transfer layer, and said charge transfer layer constitutes the exposed upper surface of the photosensitive element.

4. An electrophotographic element according to claim 1, wherein the thickness of said charge carrier generating layer is 5μ or less, and the thickness of said charge transfer layer is the range of from 3 to 50μ.

5. An electrophotographic element according to claim 4, wherein the thickess of said charge carrier generating layer is in the range of from 0.01 to 0.5μ, and the thickness of said charge transfer layer is in the range of from 5 to 20μ.

6. An electrophotographic element according to claim 1, wherein said charge carrier generating layer contains a charge carrier generating material selected from the group consisting of selenium and alloys thereof, disazo pigments, trisazo pigments and perylene pigments.

7. An electrophotographic element according to claim 1, wherein said charge carrier generating layer contains a charge carrier generating material selected from the group consisting of disazo pigments having biphenyl skeleton, disazo pigments having carbazole skeleton, trisazo pigments having triphenylamine skeleton, disazo pigments having styrylstilbene skeleton, disazo pigments having oxadiazole skeleton and disazo pigments having fluorenone skeleton.

8. An electrophotographic element according to claim 1, wherein said binder is selected from the group consisting of polyamide, polyurethane, polyester, epoxy resin, polyketone, polycarbonate, polyvinylketone, polystyrene, poly-N-vinylcarbazole, polyacrylamide, acryl resin and polyvinylacetal.

9. An electrophotographic element which comprises an electrically conductive substrate, and a charge carrier generating layer and a charge transfer layer superposed on said substrate, said charge carrier generating layer containing a charge carrier generating material selected from the group consisting of disazo pigments having biphenyl skeleton, disazo pigments having carbazole skeleton, disazo pigments having styrylstilbene skeleton, disazo pigments having oxadiazole skeleton and disazo pigments having fluorenone skeleton, and said charge transfer layer contains at least one hydrazone compound having the general formula:

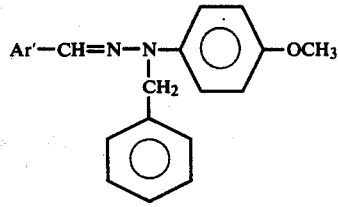

wherein Ar' is selected from the group consisting of styryl, α-methyl styryl, methoxy-substituted styryl and dimethylamino-substituted styryl;
and a binder.

10. An electrophotographic element according to claim 9, wherein said hydrazone compound is selected from the group consisting of:

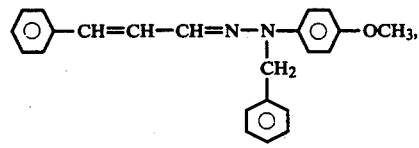

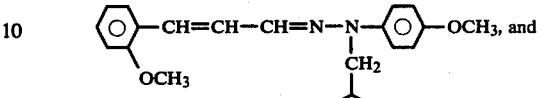

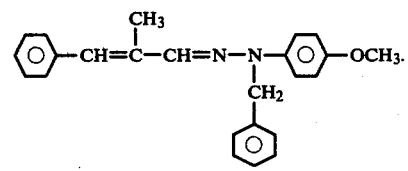

* * * * *

UNITED STATES PATENT AND TRADEMARK OFFICE
CERTIFICATE OF CORRECTION

PATENT NO. : 4 385 106
DATED     : May 24, 1983
INVENTOR(S) : Kiyoshi Sakai

It is certified that error appears in the above-identified patent and that said Letters Patent is hereby corrected as shown below:

Column 20, line 18; change that portion of formula to read as follows:

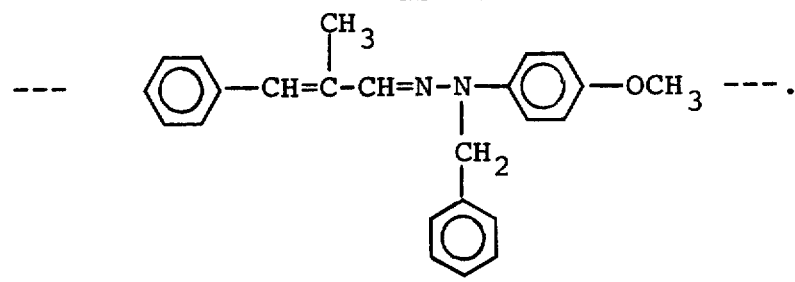

Signed and Sealed this

Third Day of April 1984

[SEAL]

Attest:

GERALD J. MOSSINGHOFF

Attesting Officer

Commissioner of Patents and Trademarks